United States Patent [19]

Riccitelli et al.

[11] Patent Number: 5,054,882

[45] Date of Patent: Oct. 8, 1991

[54] MULTIPLE OPTICAL FIBER EVENT SENSOR AND METHOD OF MANUFACTURE

[75] Inventors: Samuel D. Riccitelli, Murrieta; Thomas A. Shern, San Diego, both of Calif.

[73] Assignee: Puritan-Bennett Corporation, Carlsbad, Calif.

[21] Appl. No.: 565,495

[22] Filed: Aug. 10, 1990

[51] Int. Cl.⁵ .................................................. G02B 6/16
[52] U.S. Cl. .................................... 385/12; 606/16; 385/902
[58] Field of Search ............... 350/96.10, 96.15, 96.29, 350/96.30, 320; 606/2, 10-12, 15, 16

[56] References Cited

U.S. PATENT DOCUMENTS

| | | | |
|---|---|---|---|
| 4,321,057 | 3/1982 | Buckles | 23/230 B |
| 4,399,099 | 8/1983 | Buckles | 422/58 |
| 4,682,895 | 7/1987 | Costello | 350/96.29 X |
| 4,706,677 | 11/1987 | Goorsky et al. | 128/634 |
| 4,727,730 | 3/1988 | Bioarski et al. | 128/667 |
| 4,748,254 | 6/1988 | Seaver | 350/96.29 |
| 4,752,115 | 6/1988 | Murray, Jr. et al. | 350/96.29 |
| 4,830,013 | 5/1989 | Maxwell | 128/637 |
| 4,846,548 | 7/1989 | Klainer | 350/96.29 |
| 4,865,416 | 9/1989 | Pratt | 350/96.29 |
| 4,928,694 | 5/1990 | Maxwell | 128/637 |
| 4,954,318 | 9/1990 | Yafuso et al. | 350/96.29 X |

FOREIGN PATENT DOCUMENTS

| | | |
|---|---|---|
| 0245073 | 11/1987 | European Pat. Off. |
| 303883A1 | 10/1980 | Fed. Rep. of Germany |
| 2108675A | 4/1982 | United Kingdom |

OTHER PUBLICATIONS

Mahutte et al., "Progress in the Development of a Fluorescent Intravascular Blood Gas System in Man", *The Journal of Clinical Monitoring*, vol. 6, No. 2, Apr., 1990, pp. 147-157.

*Primary Examiner*—John D. Lee
*Attorney, Agent, or Firm*—Fulwider, Patton, Lee & Utecht

[57] ABSTRACT

The multiple optical fiber event sensor apparatus includes a semi-permeable tubular sleeve, and a plurality of individual optical fiber event sensor modules within the sleeve arranged in an axially staggered relationship. A rounded tip is also provided on the distal end of the sleeve. The device provides for a multiplicity of individual sensors incorporated in a single tubular sleeve which minimizes cross-interference and thrombus formation when used as an intravascular multi-sensor.

19 Claims, 1 Drawing Sheet

MULTIPLE OPTICAL FIBER EVENT SENSOR AND METHOD OF MANUFACTURE

BACKGROUND OF THE INVENTION

1. Field of the Invention

This invention is generally directed to chemical and biochemical analysis for an analyte in a fluid or gaseous mixture, and more specifically concerns a multiple event sensor for performing analysis of multiple analytes, and a method of manufacturing the multiple event sensor.

2. Description of Related Art

Measurement of acidity (pH) and the tension or partial pressure of carbon dioxide and oxygen in the blood have become particularly important in modern medicine in determining the respiratory status of a patient. Optical sensors have been developed which are based upon the principle of quenching of the fluorescence reaction of certain dye indicators in the presence of the analyte of interest. The fluorescent indicator is typically immobilized within a permeable membrane on the end of an optical fiber utilized in measuring the intensity of the fluorescence reaction of the indicator at a certain emission wavelength. Another optical fiber may also be used to carry a certain wavelength of light to initiate the fluorescence of the indicator, although it is possible to reduce the size of the sensor by using the same optical fiber for conducting the different wavelengths of fluorescence and excitation light.

Although a fiber optic fluorosensor for oxygen and carbon dioxide has been developed which includes a first indicator layer sensitive to oxygen and a second indicator layer sensitive to carbon dioxide on a single optical fiber, such multiple layer optical fiber sensors can be difficult to manufacture, and there is a concern that such an arrangement of indicator layers may interfere with the sensitivity of one or more of the indicator layers in the sensor. A triple sensor for blood pH, $pCO_2$, and $pO_2$ has also been developed which includes three separate optical fibers having appropriate indicator layers at their ends, but possible cross-interference of the individual sensor layers on ends of the optical fibers remains a matter of concern; and overlap of the ends of the optical fibers which tend to be the thickest portion of the optical fiber sensors, affecting the shape of the sensor, tends to increase the risk of development of thrombus buildup with intravascular use of the device.

Hence, it would be desirable to provide a multiple blood gas sensor which combines various, individual proven sensors into a single apparatus which minimizes cross-interference of individual sensors within the apparatus, and achieves a shape which minimizes turbulence of blood as it flows by the device when it is used intravascularly.

SUMMARY OF THE INVENTION

Briefly and in general terms, a multiple optical fiber event sensor apparatus according to the present invention includes a semi-permeable tubular sleeve, and a plurality of individual optical fiber event sensor modules within the sleeve arranged in an axially staggered relationship. A rounded tip is also provided on the distal end of the sleeve. The device provides for multiple individual fluorescent blood gas sensors incorporated in a single tubular sleeve which is easily manufacturable, properly shaped to avoid thrombogenicity, and structurally sound to withstand the rigors of intravascular placement.

Other aspects and advantages of the invention will become apparent from the following detailed description, taken in conjunction with the accompanying drawing, which illustrates, by way of example, the principles of the invention.

DETAILED DESCRIPTION OF THE PREFERRED EMBODIMENT

Figure 1:
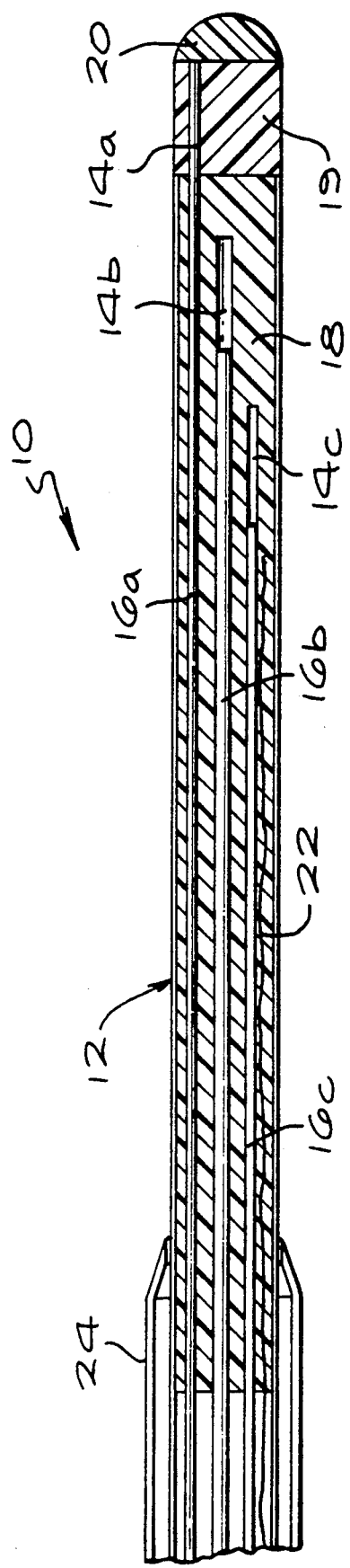
FIG. 1 is an enlarged longitudinal cross-section of the multiple optical fiber event sensor of the invention.

Problems of structural instability, thrombogenicity, and cross-interference of individual optical fiber fluorosensors have been observed in multiple blood gas sensors. In the multiple optical fiber event sensor of the invention, axially staggering individual sensors within a tubular sleeve, fixing the individual sensors in position, and forming a rounded tip at the end of the tubular sleeve provide such a multiple sensor with structural integrity, an optimal nonthrombogenic shape for intravascular use, and a minimum of cross-interference among the individual sensors.

As is shown in the drawings which are provided for purposes of illustration, the invention is preferably embodied in a multiple optical fiber event sensor 10, having a tubular sleeve 12, which is preferably formed of a polymeric material which is permeable to the analyte of interest, and not permeable to matter in the blood which it would be desirable to exclude from the sensor. The sleeve is preferably formed from a silicone polymer to have a very thin wall less than about 0.010 inches thick, and preferably less than about 0.002 inches thick. Other materials which have good mechanical properties, which are gas and/or ion permeable, and which are blood and bio-compatible, may also be suitable. A bundle of analyte sensor modules 14a,b,c, which may for example be pH, $pCO_2$ and $pO_2$ sensors, mounted on the distal ends of optical fibers 16a,b,c, are disposed within the sleeve. The sleeve is typically sized so that the inside diameter is only slightly larger than the diameter of the sensor bundle. The sensor bundle is threaded into the sleeve, which may be facilitated by expanding the sleeve by applying a vacuum to the outer surface of the sleeve and/or increasing the internal pressure within the sleeve. Once the sensor bundle has been threaded into the sleeve, the sensor modules on the distal ends of the individual optical fiber sensors are staggered axially within the sleeve. The sensor modules are preferably axially staggered by sliding the optical fibers such that no one sensor module is directly adjacent any portion of any other sensor module. This prevents stacking of the active sensor portions which typically have the thickest diameter of any portion of the optical fiber sensors, since the tip is the region where the chemical indicators are applied. It has been found that it is important to prevent the occurrence of bulges on the surface of the sleeve which may induce turbulent blood flow, which thereby may lead to thrombus formation on the surface of the device when used intravascularly. Staggering the sensors axially in this fashion provides the sleeve with a smooth, cylindrical surface, minimizing the risk of thrombus formation.

Once the bundle of sensors has been threaded into the sleeve and staggered axially within the sleeve, they are potted into place with a polymeric potting compound matrix 18, which is currently preferably a hydrophobic silicone polymer. Other materials, such as various hydrogels and polyurethanes may also be used. The potting compound should adhere well to the sleeve, should be gas and/or ion permeable, and should be blood and bio-compatible. The potting compound may fill all or only a portion of the sleeve. If a pH sensor such as sensor 14a is included in the sensor bundle, a layer of hydrophilic potting compound 19 such as a hydrogel or polyurethane, preferably surrounds the pH sensor to allow ions from the blood to reach the sensor. Alternatively, an opening in the matrix 18, or a tube through it could be formed in the matrix to provide an ion flow path to the pH sensor.

A polymeric tipping compound matrix 20 is also preferably applied, either after application of the potting compound, or in the same step as applying the potting compound. The tipping compound may be of the same material used for the potting compound. Although a hydrophobic silicone polymer is a currently preferred tipping compound, various hydrogels and polyurethane, or other suitable materials, may also be used. When a pH sensor is included in the sensor bundle, the tipping compound is preferably hydrophilic, to facilitate the passage of blood ions to the pH sensor. The tipping compound is shaped to form the rounded tip, which extends outward beyond the distal end of the sleeve, to achieve the overall smooth and rounded shape of the device. The tipping compound is preferably applied in a manner so as to avoid the formation of any dead spaces, voids, or bulges in the rounded tip. This configuration has been tested in vivo, in dogs, pigs, baboons, and in humans, with no evidence of thrombus having been observed.

Other types of sensors may also be included in the multiple optical fiber event sensor, such as a thermocouple 22, useful for measuring patient temperature. The apparatus may be introduced into the vasculature of a patient by an introducer catheter 24, a guiding catheter, or other suitable means. Other types of sensors such as electrodes may also be incorporated into the multiple optical fiber event sensor.

Figure 2:
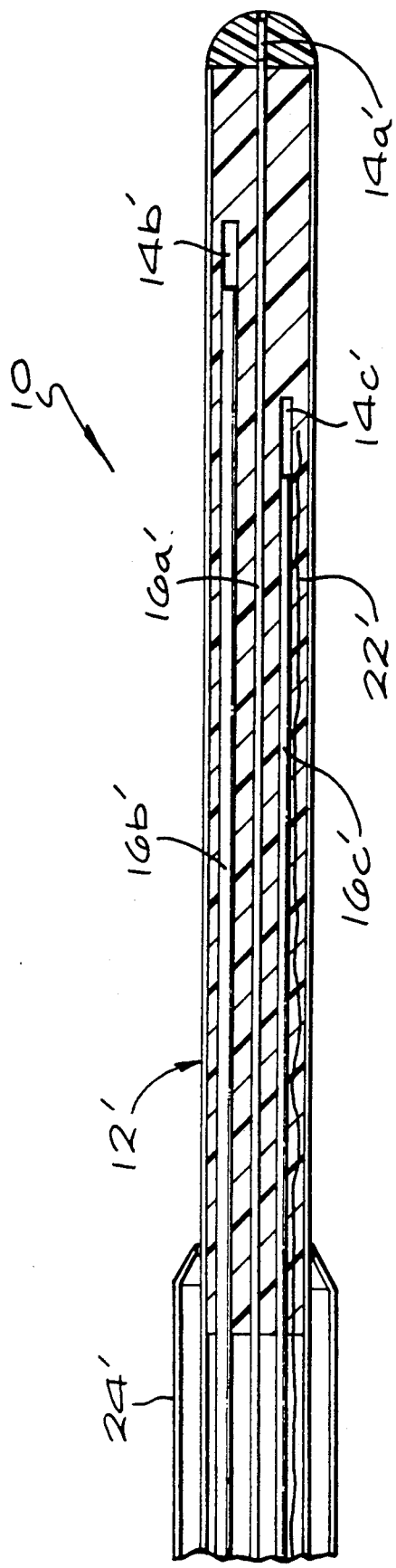
FIG. 2 is an enlarged longitudinal cross-section of a second embodiment of the invention.

Another embodiment of the multiple optical fiber event sensor similar to that of FIG. 1 is illustrated in FIG. 2. In this embodiment, the multiple optical fiber event sensor 10' also includes a tubular sleeve 12', which is preferably formed of a semipermeable polymeric material such as a silicone polymer having a thin wall less than or equal to about 0.010 inches thick and preferably less than or equal to about 0.002 inches thick. The bundle of analyte sensor modules may include a pH sensor 15a', a pCO$_2$ sensor 14b', and a pO$_2$ sensor 14c', mounted on the distal ends of optical fibers 16a', b', c', respectively, within the sleeve. The sensor modules are preferably axially staggered as in the first embodiment, except that the pH sensor 14a' extends beyond the potting compound matrix 18', which is also typically a hydrophobic silicone polymer, into polymeric tipping compound matrix 20'. Either the matrix surrounding the pH sensor must be hydrophilic, or a flow path such as an opening or tube in the matrix must be provided, to admit ions from the blood to the sensor. In the currently preferred alternate embodiment, the polymeric tipping compound 20' in which the pH sensor is embedded is hydrophilic, such as a hydrogel or polyurethane. The apparatus may be introduced into the vasculature of a patient by an introducer catheter 24', a guiding catheter, or other suitable means.

From the foregoing, it will be appreciated that the invention provides a multiple event sensor apparatus with individual sensors incorporated in a single tubular sleeve which is easily manufacturable and structurally sound. The axial staggering of the optical fiber sensors serves to minimize potential problems of cross-interference of the sensors, and allows the sleeve of the multiple sensor to be smoothly shaped so that in combination with the rounded tip, thrombus formation is minimized when the device is used intravascularly.

While a particular form of invention has been illustrated and described, it will be apparent that various modifications can be made without departing from the spirit and scope of this invention. Accordingly, it is not intended that the invention be limited, except as by the appended claims.

What is claimed is:

1. A multiple optical fiber event sensor apparatus, comprising:
   a semi-permeable tubular sleeve having proximal and distal ends;
   a plurality of optical fiber gas sensors, each having a distal end bearing a sensor module, said sensor modules being disposed within said sleeve in axially staggered relationship; and
   a semi-permeable polymeric matrix having a hydrophobic portion surrounding said sensor modules of said gas sensors for fixing the position of said sensor modules within said sleeve and substantially filling said sleeve; and
   a rounded tip formed of said polymeric matrix extending beyond the distal end of said sleeve.

2. The apparatus of claim 1, wherein said tubular sleeve comprises silicone and has a tubular wall less than about 0.010 inches thick.

3. The apparatus of claim 1, wherein said tubular sleeve comprises silicone and has a tubular wall less than about 0.002 inches thick.

4. The apparatus of claim 1, wherein said optical fiber gas sensors comprise a blood oxygen sensor, and a blood carbon dioxide sensor, and further including a blood pH sensor, said blood pH sensor disposed within a hydrophilic portion of said polymeric matrix adjacent to a distal end of said hydrophobic portion of said polymeric matrix.

5. The apparatus of claim 4, wherein said hydrophilic polymeric matrix portion is selected from the group consisting of hydrogel, and polyurethane.

6. The apparatus of claim 1, wherein said hydrophobic polymeric matrix portion is formed from silicone.

7. The apparatus of claim 1, further including a temperature sensor disposed within said sleeve.

8. The apparatus of claim 1, wherein said rounded tip is formed without voids.

9. An intravascular multiple event sensor apparatus, comprising:
   a semi-permeable tubular member having proximal and distal ends;
   a plurality of optical fiber sensors including an oxygen sensor and a carbon dioxide sensor having proximal and distal ends, the distal ends of said optical sensors being disposed within said tubular member, each said optical fiber distal end having an event sensor module mounted thereon, said event sensor modules being disposed within said tubular member in axially staggered relationship;

a hydrophobic semi-permeable polymeric matrix disposed within and extending to the distal end of said tubular member at least partially filling said tubular member, said event sensor modules being disposed within said hydrophobic matrix and fixing the position of said event sensor modules within said tubular member; and a hydrophilic semi-permeable polymeric matrix disposed on the distal end of said tubular member forming a rounded tip extending beyond the distal end of said tubular member.

10. The apparatus of claim 9, wherein said tubular member comprises silicone and has a tubular wall less than about 0.010 inches thick.

11. The apparatus of claim 9, wherein said tubular member comprises silicone and has a tubular wall less than about 0.002 inches thick.

12. The apparatus of claim 9, further including a blood pH sensor.

13. The apparatus of claim 9, wherein said hydrophobic polymeric matrix consists essentially of silicone and said hydrophilic polymeric matrix is selected from the group consisting of hydrogel, and polyurethane and combinations thereof.

14. The apparatus of claim 9, wherein said rounded tip is formed without voids.

15. The apparatus of claim 9, further including a temperature sensor disposed within said tubular member.

16. A method of making a multiple optical fiber event sensor apparatus having a plurality of optical fiber gas sensors each having a distally mounted event sensor module, comprising the steps of:

placing said event sensor modules of said optical fiber gas sensors within a semipermeable tubular sleeve in axially staggered relationship;

fixing the position of said even sensor modules of said gas sensors within said sleeve by placing a semipermeable polymeric potting matrix around said sensor modules; and forming a rounded tip extending beyond the distal end of the sleeve.

17. The method of claim 16, wherein the step of fixing the position of said event sensors comprises packing a hydrophobic polymeric matrix around said event sensor modules within a proximal portion of said sleeve and a hydrophilic polymeric matrix at the distal end of said sleeve.

18. The method of claim 16, wherein said step of forming said rounded tip comprises placing a second polymeric matrix on the distal end of said sleeve and forming said rounded distal tip from said second polymeric matrix.

19. The method of claim 16, wherein said rounded tip is formed without voids.

* * * * *